US008418881B2

(12) United States Patent
Kerrod et al.

(10) Patent No.: US 8,418,881 B2
(45) Date of Patent: Apr. 16, 2013

(54) TISSUE CASSETTE DISPENSING APPARATUS

(75) Inventors: Ian Kerrod, Flintshire (GB); Richard Clarkson, Leyland (GB); Basil Gaynor, Holmes Chapel (GB)

(73) Assignee: Thermo Shandon Ltd., Cheshire (GB)

( * ) Notice: Subject to any disclaimer, the term of this patent is extended or adjusted under 35 U.S.C. 154(b) by 785 days.

(21) Appl. No.: 12/234,062

(22) Filed: Sep. 19, 2008

(65) Prior Publication Data

US 2009/0145920 A1   Jun. 11, 2009

(30) Foreign Application Priority Data

Sep. 21, 2007   (GB) .................................. 0718610.9

(51) Int. Cl.
*B65H 1/00* (2006.01)
*B65H 3/00* (2006.01)

(52) U.S. Cl.
USPC ........... 221/197; 221/258; 221/268; 221/210; 221/259; 221/248; 221/198; 221/1; 221/209; 221/276; 221/2; 221/21; 221/124; 221/126; 221/232; 221/289; 221/271; 221/272; 221/270

(58) Field of Classification Search .................. 221/268, 221/210, 259, 248, 198, 1, 209, 276, 2, 21, 221/124, 126, 232, 197, 289, 271, 272, 258, 221/270

See application file for complete search history.

(56) References Cited

U.S. PATENT DOCUMENTS

| | | | | |
|---|---|---|---|---|
| 2,263,040 A * | 11/1941 | Kaltenbach | ................... | 221/213 |
| 3,833,148 A * | 9/1974 | Honas | ........................... | 221/250 |
| 3,957,175 A * | 5/1976 | Gordon | ......................... | 221/215 |
| 4,013,179 A * | 3/1977 | Fluck | .......................... | 414/796.1 |
| 4,085,863 A * | 4/1978 | Johnson | .......................... | 221/20 |
| 4,542,834 A * | 9/1985 | Kurosawa et al. | ............. | 221/116 |
| 5,511,690 A * | 4/1996 | Calhoun et al. | ................ | 221/197 |
| 5,842,598 A * | 12/1998 | Tsuchida | ........................ | 221/258 |
| 5,941,414 A * | 8/1999 | Kasper | ........................... | 221/210 |
| 6,098,839 A * | 8/2000 | Hunnell | ........................ | 221/197 |
| 6,098,840 A * | 8/2000 | Ito et al. | .......................... | 221/232 |
| 6,889,869 B2 * | 5/2005 | Hallin | ........................... | 221/223 |
| 7,172,116 B2 * | 2/2007 | Yamamiya | ..................... | 235/381 |
| 2003/0059281 A1 * | 3/2003 | Kiene et al. | ........................ | 414/1 |
| 2010/0084419 A1 * | 4/2010 | Haas et al. | ......................... | 221/1 |

FOREIGN PATENT DOCUMENTS

| | | |
|---|---|---|
| GB | 2 304 704 | 3/1997 |
| GB | 2 308 841 | 7/1997 |
| WO | WO-02/21144 | 3/2002 |

OTHER PUBLICATIONS

Extended European Search Report for European Application No. 08 25 3079, Apr. 5, 2012, European Patent Office, The Hague, Netherlands.

* cited by examiner

*Primary Examiner* — Gene O. Crawford
*Assistant Examiner* — Rakesh Kumar
(74) *Attorney, Agent, or Firm* — Stites & Harbison PLLC; Marvin Petry

(57) ABSTRACT

The present invention aims to provide a dispensing apparatus for dispensing individual tissue cassettes from a stack of cassettes, the apparatus includes a hopper for receiving a stack of tissue cassettes, the hopper having an aperture through which cassettes are dispensable; ejection means for ejecting a cassette through the aperture; and retention means for retaining all but one of the cassettes in the stack as an individual cassette is ejected.

16 Claims, 13 Drawing Sheets

TISSUE CASSETTE DISPENSING APPARATUS

The present invention relates to tissue cassettes and to an apparatus and method for dispensing such tissue cassettes.

Tissue cassettes are small trays used for holding samples of tissue for analysis. Typically the tissue is human tissue (although it may be animal tissue) which may have been taken from a patient for the purposes of performing analysis or diagnostic tests. Generally, tissue cassettes are made of plastic and are a standard rectangular size of approximately 3 cm by 2 cm wide and approximately ½ cm deep.

Clearly tissue cassettes need to be labelled accurately e.g. with identification details (such as relating to the patient). This can be done by hand but there are also existing tissue cassette processing machines which are used to process and label large numbers of cassettes. One such machine (sold under the brand name Shandon Microwriter™) includes several hoppers. Each hopper is adapted to receive a stack of tissue cassettes and the machine has a dispensing mechanism for extracting cassettes from a hopper one at a time. Successive hoppers can be moved into position with respect to the mechanism so that cassettes can be removed from different hoppers, as required.

Cassettes are manufactured by many different manufacturers and whilst they are typically of the size and shape described above, the cassettes of different manufacturers do differ slightly in detail. However, generally users expect to be able to use cassettes produced by different manufacturers with a single machine. This can lead to problems in reliably dispensing cassettes from the hoppers since the hoppers are not necessarily designed to accommodate all types of cassettes. Therefore one typical problem is that on occasion the dispensing mechanism can become jammed.

Generally, a number of cassettes (typically 25 or 50 or 75) are supplied loaded inside a tube and it is this tube which is loaded into a hopper. The hopper is therefore appropriately sized to receive the tube but this leads to the problem that as a cassette leaves the tube the dimensions of the hopper are such that it is not held firmly within the hopper. This can lead to some variation in alignment within the hopper of a cassette which is about to be dispensed by the dispensing mechanism, which in turn increases the likelihood of possible problems such as jamming the dispensing mechanism.

Accordingly, the present invention aims to provide a tissue cassette dispensing apparatus and method which reduces some or all of these problems.

At its most general level, the dispensing mechanism of the hopper of the present invention does not rely on the cassettes stacks being self-supporting during dispensing unlike the prior art equipment. Instead, the present invention, in one aspect, incorporates means for holding all but one of the stack of cassettes in position as a single cassette is dispensed, so that the remainder of the cassette stack does not interfere with the dispensing mechanism.

Additionally or alternatively, also at a general level, the present invention tackles the second problem mentioned above in a further aspect which is to provide means within the hopper for retaining a cassette or cassettes in a suitable alignment position once the cassette(s) has been removed from its storage tube.

Accordingly, in a first aspect, the present invention provides dispensing apparatus for dispensing individual tissue cassettes from a stack of such cassettes, the apparatus including:

a hopper for receiving a stack of tissue cassettes, the hopper having an aperture through which cassettes are dispensable;

ejection means for ejecting a cassette through the aperture;

retention means for retaining all but one of the cassettes in the stack as an individual cassette is ejected.

In this way, as mentioned previously, the retention means prevents or reduces interference in the ejection process by the remaining cassette stack.

Preferably, the ejection means includes a tray in which a single tissue cassette may be held. The tray is moveable so as to be useable to transport a tissue cassette away from the stack of cassettes when a cassette is to be dispensed. Preferably, the tray is arranged such that, in normal use, a cassette may slide out of the tray under the action of gravity alone.

The hopper may be such that part of it is adapted to receive a tube inside which the cassettes are supplied. Part or most of the tube may then extend out of the hopper.

Preferably the hopper includes a pocket in which at least part of the stack of cassettes may be held in use. Preferably the retention means acts on one or more of the cassettes in the pocket. More preferably, the retention means acts on at least the lowest cassette in the pocket which when it is retained in position in the pocket by the retention means then in turn serves to hold the remainder of the cassettes in the stack in position. If the injection means incorporates a tray, the lowest cassette in the pocket will typically be the cassette next in the stack to the cassette in the tray.

In some embodiments, the retention means includes a finger or tooth which is moveable so as to grip a cassette, possibly e.g. by holding it against one or more of the walls of the pocket or hopper.

Preferably the hopper also includes gate means for closing the aperture. Such gate means act to prevent unwanted dispensing of a cassette. The gate means are openable so as to permit a cassette to be ejected through the aperture. Preferably the gate means are biased to a closed position.

Preferably the retention means is arranged in conjunction with the gate means such that when the gate means is fully open (i.e. open sufficiently to permit ejection of a cassette) the retention means is in operation to retain the remainder of the cassettes in the stack. More preferably, the opening of the gate means causes the retention means to operate as described. Preferably when the gate means is fully closed, the retention means is not operating i.e. is not retaining the cassettes in the stack in any particular position. In the example given above where the retention means includes a finger or tooth, preferably the gate means includes a member which causes the finger/tooth to engage one or more cassettes in the stack as previously described.

In the embodiments of the apparatus in which the ejection means includes a tray, the gate means may act so as to prevent a cassette from leaving the tray until/unless the gate means is fully open. In the example where the tray is slideable so as to transport a cassette within the tray away from the stack, the sliding action of the tray may open the gate means. Preferably this is accomplished simply by the tray bearing on the gate means and pushing the gate means open. In this way, the gate means progressively opens as the tray slides.

Preferably the action of the tray on the gate in turn causes the gate to operate the retention means as previously described. However, additionally or alternatively, the movement of the tray may be arranged to trigger the operation of the retention means independently of the opening of the gate means. Preferably this would achieve the same result, namely that the retention means is activated so as to retain the cassettes in the stack before the gate means is fully open so as to permit release of a cassette from the tray.

So, in one embodiment, the sequential operation of the apparatus will be as follows:

1. A plurality of cassettes are loaded into the hopper. If the cassettes are supplied in a cassette tube, then part of the cassette tube may be inserted into a portion of the hopper so that cassettes can exit from the tube into the pocket, preferably under the action of gravity alone.
2. The lowermost cassette in the stack exits from the pocket to a location where it may be acted upon by the ejection means. That location may be a tray.
3. When it is wished to dispense a cassette, the ejection means acts so as to move a single cassette away from the stack. This may be by movement of the tray.
4. Before the cassette being dispensed is fully dispensed, the retention means acts so as to retain the remainder of the cassettes in the stack so as to reduce any interference by the remaining stack on the dispensing operation. This may be activated by operation of the gate means, which in turn activates the retention means, which acts e.g. on the lowest remaining cassette in the stack.
5. Once the dispensing operation is completed, the retention means releases the cassette(s) which were being held in position, so as to permit the next cassette in the stack to move into the position in which it can subsequently be acted on by the ejection means. In one example, this is achieved by the tray being returned to its rest position, which in turn permits the gate means to close which in turn permits the retention means to release the cassette previously retained. The whole remaining stack then moves downwards.

As previously mentioned, the rejection means may include a tray. The tray may further include separation means for improving the separation of the cassette held within the tray from the adjacent cassette (i.e. the next lowest cassette in the stack) as the tray is moved. This helps prevent the problem mentioned previously whereby two cassettes are attempted to be dispensed together, causing a jam. Such separation means may be achieved by suitable sizing and/or shaping of one or more side walls of the tray. In particular, the rear wall of the tray (i.e. the wall opposite the end of the tray from which a cassette is removable from the tray) may be suitably sized and/or shaped. In particular, the rear wall may be angled with respect to the rear edge of a cassette (when in position in the tray) so that a first upper portion of the rear wall i.e. a portion distant from the base of the tray) is nearer to the cassette than the lower edge of the rear wall. This helps to grip the cassette in position. The upper portion referred to may be the upper edge of the rear wall of the tray. Alternatively, it may be an area of the rear wall between its upper and lower edges.

Additionally or alternatively, a second upper portion of the rear wall of the tray may be angled in the opposite direction i.e. angled so that the lower part of that upper portion is nearer to the cassette in the tray than another part of that upper portion. This then acts as a wedge, so as to lift the adjacent cassette in the stack away from the cassette in the tray as the tray moves. This second upper portion may be further from the base of the tray than the first upper portion, if both are included.

As mentioned previously, the present invention has a second aspect which addresses the problem of the cassettes not being retained accurately in position in the hopper once the cassettes have been removed from a cassette tube.

Accordingly, in a second aspect, the present invention provides dispensing apparatus for dispensing individual tissue cassettes from a stack of such cassettes, the apparatus including:

a hopper for receiving a stack of tissue cassettes, the hopper having an aperture through which cassettes are dispensable;

ejection means for ejecting a cassette through the aperture;

the hopper including a pocket for receiving part of the stack of cassettes;

whereby at least one wall of the pocket is provided with holding means for retaining one or more cassettes in a desired position.

Preferably the holding means protrude away from the wall of the pocket so as to constrict the available space for the cassette(s) between the pocket walls. Preferably a pair of opposing side walls of the pocket are provided with holding means. In one example, such holding means consist of protuberances, preferably opposing protuberances.

Practically, the side walls of the hopper may be dimensioned so as to be suited to receive a cassette tube as previously mentioned. The side walls of the hopper may also include one or more protuberances so as to grip the cassette tube more effectively. Preferably the side walls of the pocket are in line with the side walls of the hopper and the holding means project further away from the side walls of the pocket than either the side walls of the hopper or any protuberances on the side walls of the hopper. This serves to ensure that the cassettes are better held in position once they exist from the cassette tube. By contrast, for example, if the side walls of the hopper and pocket (and any protuberances) were dimensioned the same, then clearly if the dimension is sufficient to hold the cassette tube tightly it will be too large to hold the cassettes equally tightly once they have existed from the cassette tube.

Preferably there is a gap between any protuberances on the side wall(s) of the hopper intended to be adjacent the tube in use and the holding means, i.e. the distances between opposite side walls at this gap is greater than the distance between opposite protuberances. Preferably this gap is located so that it is adjacent the lower end of a cassette tube when a cassette tube is located in the hopper. The reason for this is that sometimes the lower end of a cassette tube is slightly compressed which can inhibit the removal of cassettes from the tube. The inclusion of this gap enables the lower end of the cassette tube to expand more freely, making it easier for cassettes to exit.

The first and second aspects of the present invention may be used together or separately. In addition, in a further aspect, the present invention relates to a tissue cassette processing apparatus. The tissue cassette processing apparatus includes at least one dispensing apparatus according to either or both of the first and second aspects of the present invention. In practice, the tissue cassette processing apparatus may include a plurality of dispensing apparatuses, typically between 2 and 12, preferably between 4 and 8 and most preferably 6.

The tissue cassette processing apparatus may include ejection operating means for operating the ejection means of a dispensing apparatus. Such ejection operation means may be controlled (e.g. computer controlled) to operate the ejection means when required.

Additionally, the tissue cassette processing apparatus may include transport means for transporting either or both of the ejection operation means and the dispensing apparatus(es) in relation to each other. In one embodiment, the ejection operation means may remain stationary and the plurality of dispensing apparatuses are moveable in relation to the ejection operation means. For example, the plurality of dispensing apparatuses may be arranged on a carousel, so that the carousel can be rotated by the transport means so that the ejection operation means can operate on any of the dispensing apparatuses in turn as required.

Preferably the dispensing apparatus(es) is/are removably mounted in the tissue cassette processing apparatus. More preferably, each dispensing apparatus is removable even when it contains a whole or partial stack of tissue cassettes and preferably the whole or partial stack of tissue cassettes are retained in the hopper e.g. by the gate means. In this way, different dispensing apparatuses can be introduced to or removed from the tissue cassette processing apparatus part way through processing.

In a further aspect, the present invention also provides a method of operating a dispensing apparatus and/or a cassette processing apparatus in accordance with any one or all of the features described above.

Embodiments of the present invention will now be described by way of example, with reference to the accompany drawings in which.

Figure 1:
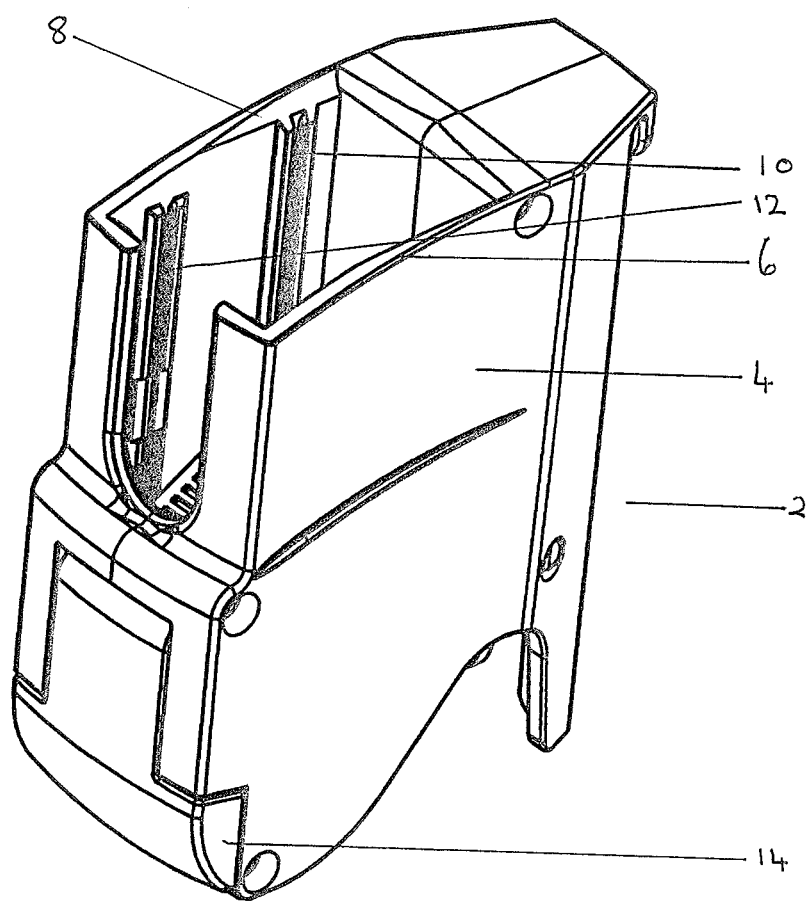
FIG. 1 shows a dispensing apparatus incorporating aspects of the present invention.

FIG. 1 shows a perspective view of a dispensing apparatus incorporating aspects of the present invention. The dispensing apparatus, which is typical referred to generally as a "cassette hopper", is indicated by numeral 2. The apparatus includes a hopper 4 for receiving a stack of tissue cassettes. Typically the cassettes will be supplied inside a cassette tube, and the hopper 4 includes side walls 6, 8 which are mutually dimensioned and located so as to receive the cassette tube. The side walls 6, 8 include protuberances 10, 12 (in this view such protuberances can only be seen on sidewall 8, but similar protuberances may also be included on the inner side of sidewall 6) to help hold the cassette tube more firmly in position.

The dispensing apparatus also includes an aperture through which cassettes are dispensable and, in this view, the aperture is closed by a door or gate 14.

Figure 2:
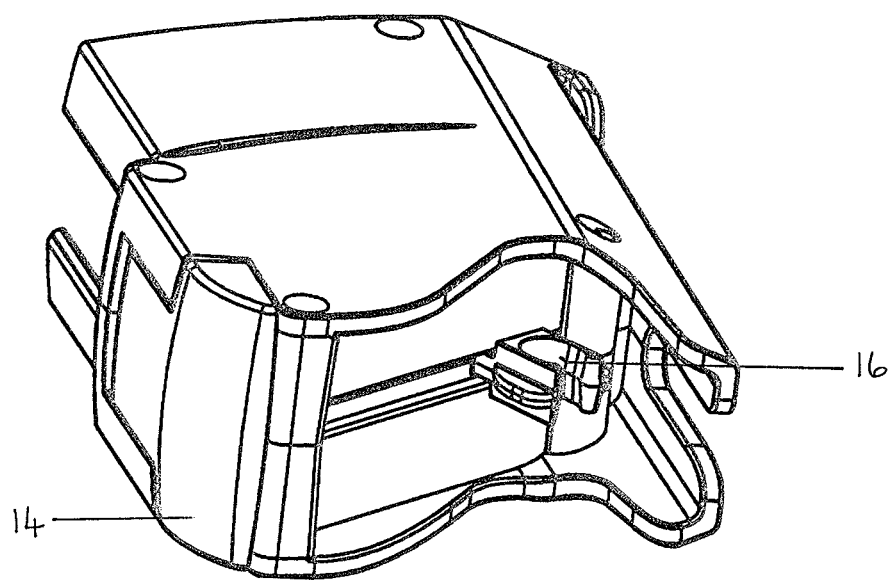
FIG. 2 shows a bottom view of the dispensing apparatus of FIG. 1.
Figure 3:
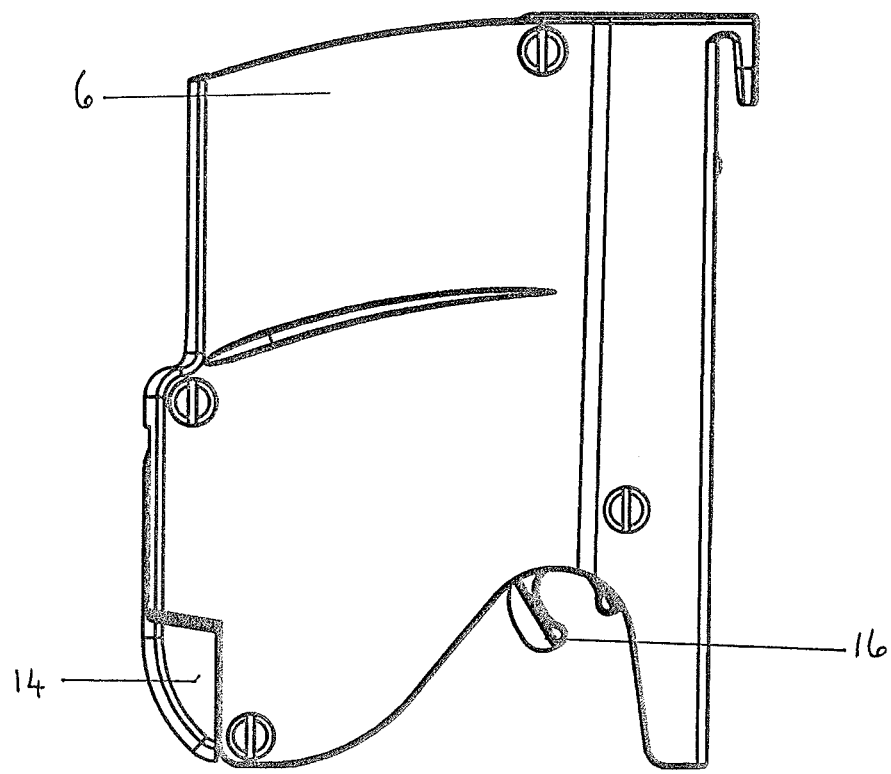
FIG. 3 shows a side view of the dispensing apparatus of FIG. 1.

FIG. 2 is a view of the bottom of the dispensing apparatus of FIG. 1 and shows an engagement member 16 which is part of the ejection means for ejecting a cassette though the aperture. The engagement member 16 can also be seen clearly in FIG. 3.

Figure 4:
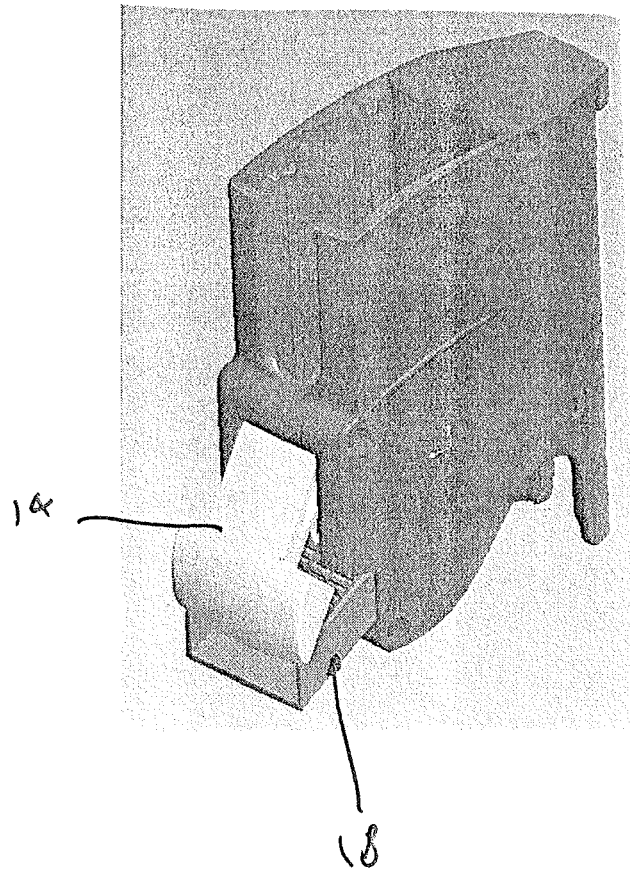
FIG. 4 shows a view of the dispensing apparatus of FIG. 1 with the tray partially slid out.

As can be seen in FIG. 4, the ejection means also includes a downwardly sloped tray 18 which, in this example, is slideably mounted so as to be moveable to protrude or partially protrude from the dispensing apparatus. The tray 18 is operably connected to the engagement member 16 such that movement of the engagement member 16 moves the tray. In addition, as seen in FIG. 4, movement of the tray also pushes on the door 14 causing the door 14 to open.

Figure 11:
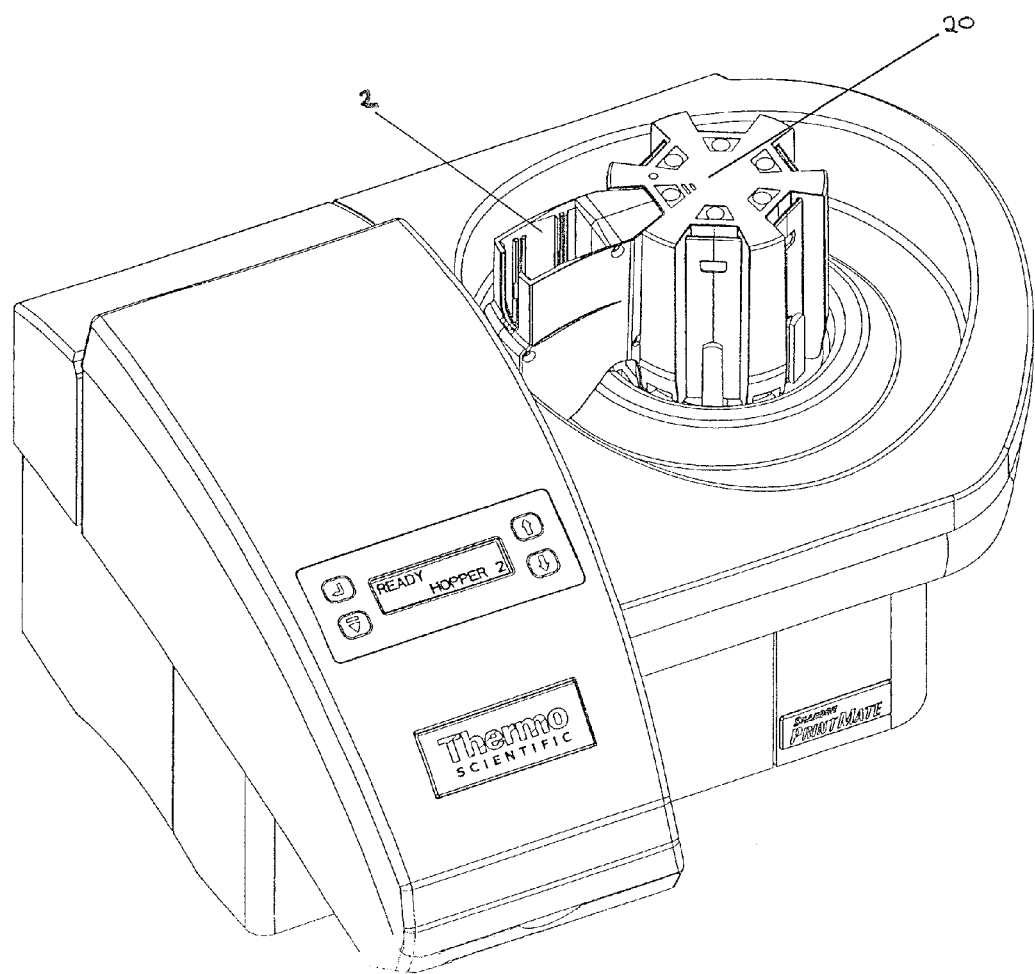
FIG. 11 is a general perspective view of the tissue cassette processing apparatus of FIG. 9.

In one aspect of the invention, the dispensing apparatus of FIGS. 1-4 is incorporated into a tissue cassette processing apparatus as shown in FIG. 11. The tissue cassette processing apparatus includes a carousel 20 onto which a plurality of dispensing apparatuses may be mounted. In FIG. 11, only one dispensing apparatus is shown mounted, but the particular carousel shown has the capacity to hold up to six such dispensing apparatuses. The carousel 20 is moveable (e.g. rotatable) so as to be useable to locate each dispensing apparatus in a desired position as required. The tissue cassette processing apparatus may include one or more ejector operator means(and typically may include only one ejector operator means) which is useable to eject a cassette from a dispensing apparatus by operating the ejecting means of that dispensing apparatus. This will be described in more detail with reference to FIG. 12 once the operation of a single dispensing apparatus has been described. The carousel 20 is operable by indexing means or transport means so as to locate a desired dispensing apparatus in the correct position so that the transport mechanism is useable with respect to that dispensing apparatus.

FIGS. 5-8 show a sectional view through the dispensing apparatus of FIGS. 1-4, illustrating the sequential operation of the dispensing apparatus.

Figure 5:
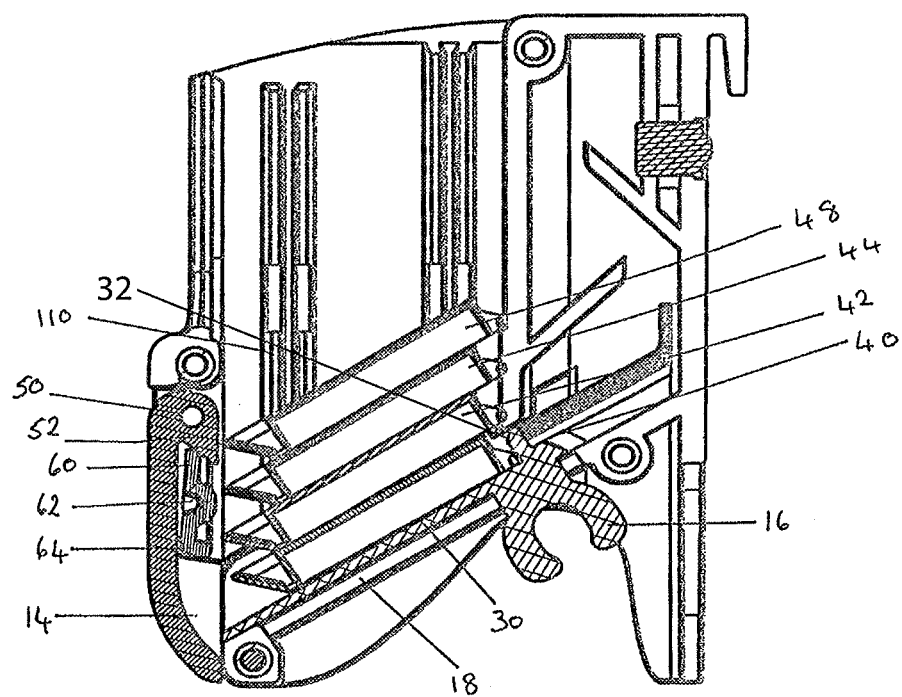
FIGS. 5 to 8 show a cross-sectional side view through the dispensing apparatus of FIG. 1-4 with the progressive operation of the apparatus illustrated.

In FIG. 5, the dispensing apparatus is in the "rest" or "closed" position. In this position, the dispensing apparatus may be separate from a tissue cassette processing apparatus, and is in a suitable state to be removed from or introduced into e.g. the carousel of a tissue cassette processing apparatus. In FIG. 5, the presence of any tissue cassette tube has been omitted for clarity, but the position of such a tube (when used) can be seen in FIGS. 9a and 10 later.

FIG. 5 clearly shows the tray 18 connected to the engagement member 16. The tray includes a base 30 and an end wall 32. A stack of four cassettes 40, 42, 44, and 48 can be seen in FIG. 5. The lowest cassette 40 is located in the tray 18 and, in this state, the remainder of the cassettes rest on the lowest cassette 40.

In FIG. 5, the door 14 is in the closed position. The door 14 is arranged to be rotatable around pivot 50 but other mechanisms for operating the door may be envisaged. The door 14 may be biased to a closed position by biasing means (not shown) e.g. a spring.

In addition, the door is operably connected to the rotation means. In this example, this is achieved by door 14 including a bearing member 52 which is operably connected to a finger 60. The finger 60 is rotatable around pivot 62 and includes a tooth 64 which is moveable into and out of engagement with at least one of the cassettes in the stack. In this example, the engagement is with cassette 42 i.e. the cassette which is adjacent the cassette located in the tray 18. Also in this example the tooth 64 is moved into and out of engagement by rotation of the finger 64 around the pivot 62, but other mechanisms for achieving this are of course envisaged.

Figure 6:
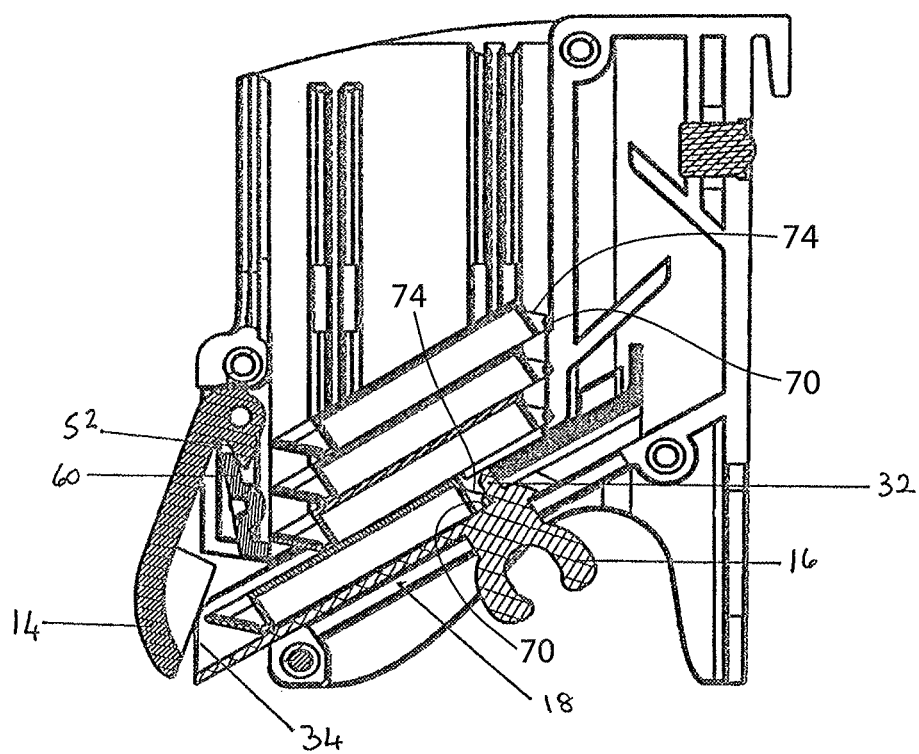

FIG. 6 shows the state of the dispensing apparatus 2 when the cassette 40 has begun to be dispensed. The engagement member 16 has been moved by e.g. the transport means of a tissue cassette processing apparatus and this has caused the downwardly sloped tray 18 to slide down to the left as seen in FIG. 6. Each cassette 40 includes a rear portion 74 with a rear corner 70. The rear wall 32 of the tray 18 bears on the rear corner 70 of cassette 40 located in the tray so as to begin to slide cassette 40 away from the rest of the stack of cassettes 42-48. A front edge 34 of tray 18 bears on door 14 so as to begin to open door 14. In turn, the bearing member 52 bears on finger 60 which begins to rotate as previously described.

Figure 7:
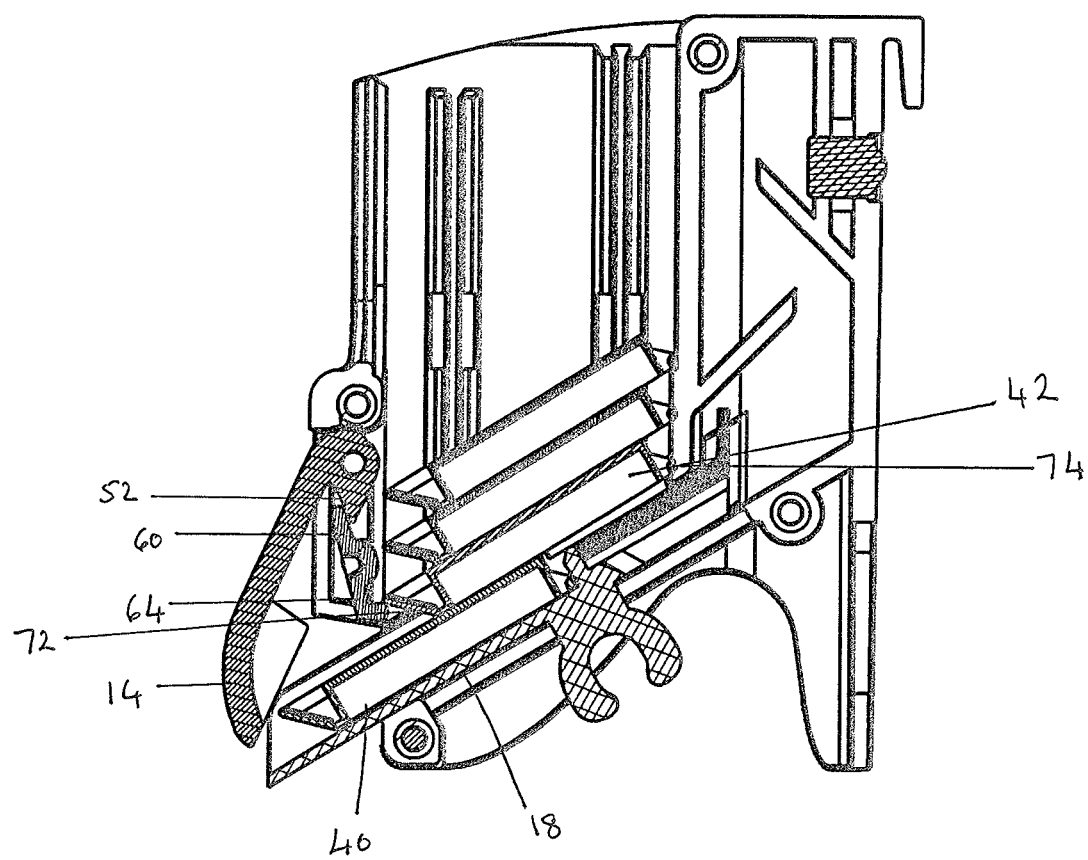

FIG. 7 then shows the state when the retention means of the dispensing apparatus has engaged but in which the cassette has not yet been dispensed. As can be seen, the tray 18 has slid further out of the hopper 4 which has caused door 14 to open yet further, but not quite yet far enough to permit cassette 40 to slide out of tray 18 under the action of gravity. However, door 14 has been moved far enough such that bearing member 52 has operated finger 60 sufficiently to engage tooth 64 with a first portion (e.g. front edge 72) of cassette 42. The action of tooth 64 also indirectly causes a pressing action on a second portion (e.g. rear portion 74) of cassette 42 against part of the hopper so as to ensure that cassette 42 remains in the hopper. This also helps reduce the pressure of cassette 42 on cassette 40, ensuring the smooth dispensing of cassette 40.

Figure 8:
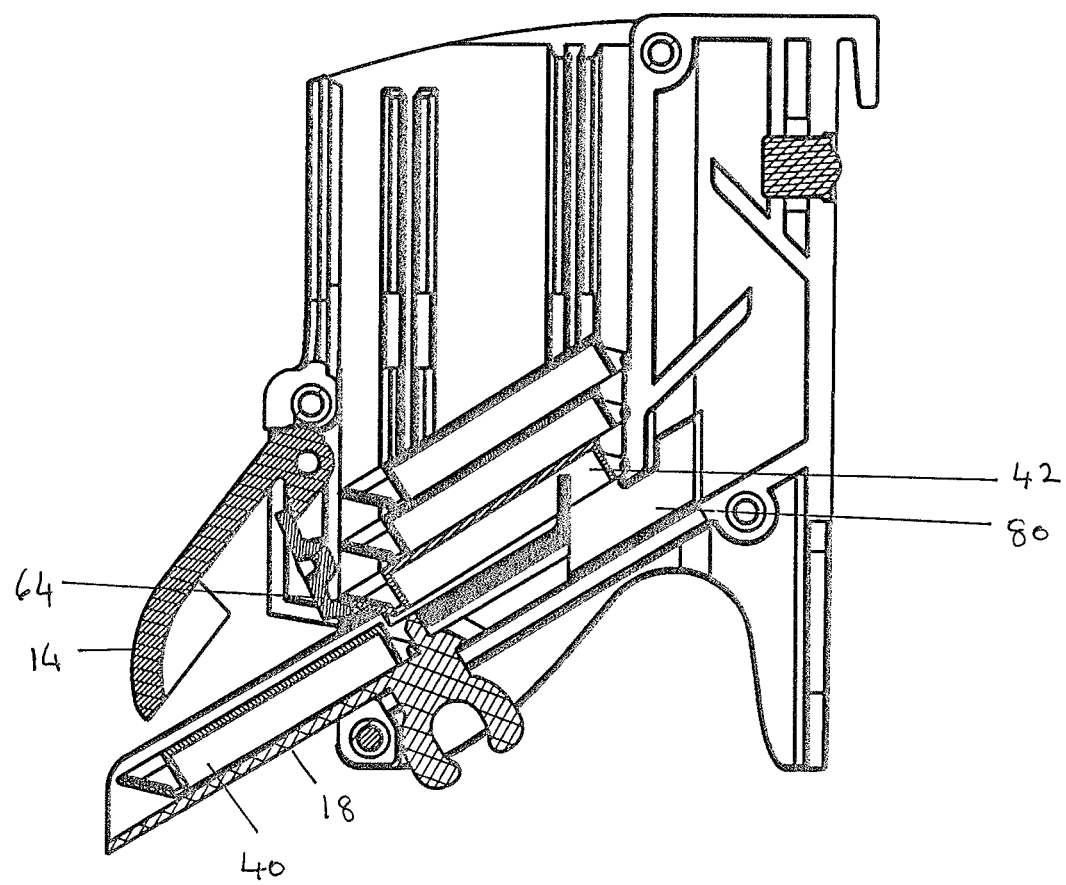

In FIG. 8, the dispensing apparatus is in the state in which cassette 40 is ready to dispense. The tray 18 has been moved far enough (e.g. to its maximum extent out of the hopper) to fully open door 14. This means that cassette 40 is free to slide out of tray 18 e.g. under the action of gravity. Typically the cassette being dispensed will slide into a portion of a cassette processing apparatus for further processing. In addition, as can be seen in FIG. 8, the tooth 64 is still engaging cassette 42 so as to retain it in position even though it is no longer supported at all by cassette 40. Optionally, to further help support the now lowest cassette 42 in the stack, the tray is operably connected to a rear support member 80. As can be seen in the sequence of FIGS. 5-8, the rear support member 80 moves progressively with the tray 18 so as to support the rear underside of cassette 42 as cassette 40 progressively moves out from under cassette 42.

As will be readily appreciated, once cassette 40 has been dispensed, the sequence shown in FIGS. 5-8 may then be reversed. In other words, tray 18 is withdrawn back into the hopper by the movement of engagement member 16. This progressively allows door 14 to close (e.g. under the action of its biasing means) which progressively releases the retention means on cassette 42. Once the retention means has been completely released, tray 18 will be back in the rest position and cassette 42 is then free to drop into tray 18 (e.g. under the action of gravity) and the apparatus is ready to repeat the process again.

Figure 9A:
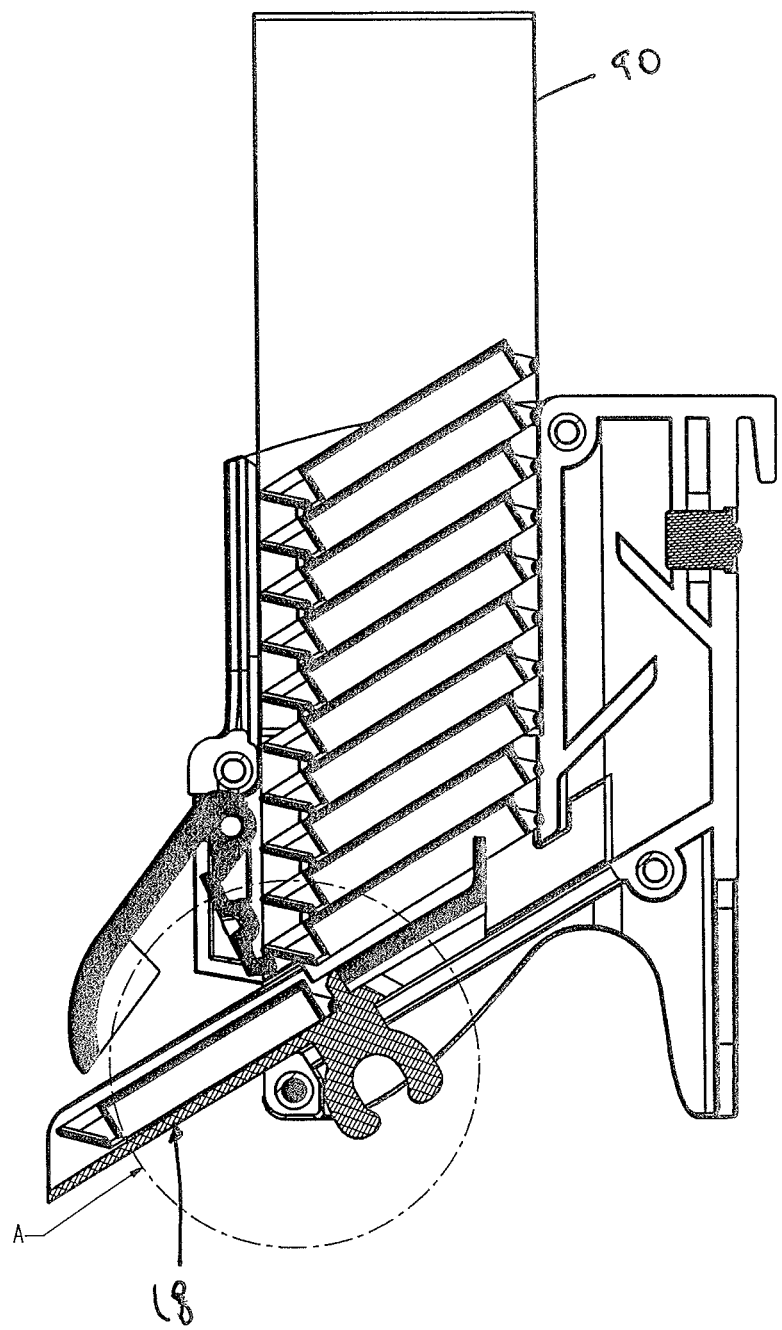
FIG. 9a shows a view of the dispensing apparatus as seen in FIG. 8, but with a cassette tube in place.
Figure 10:
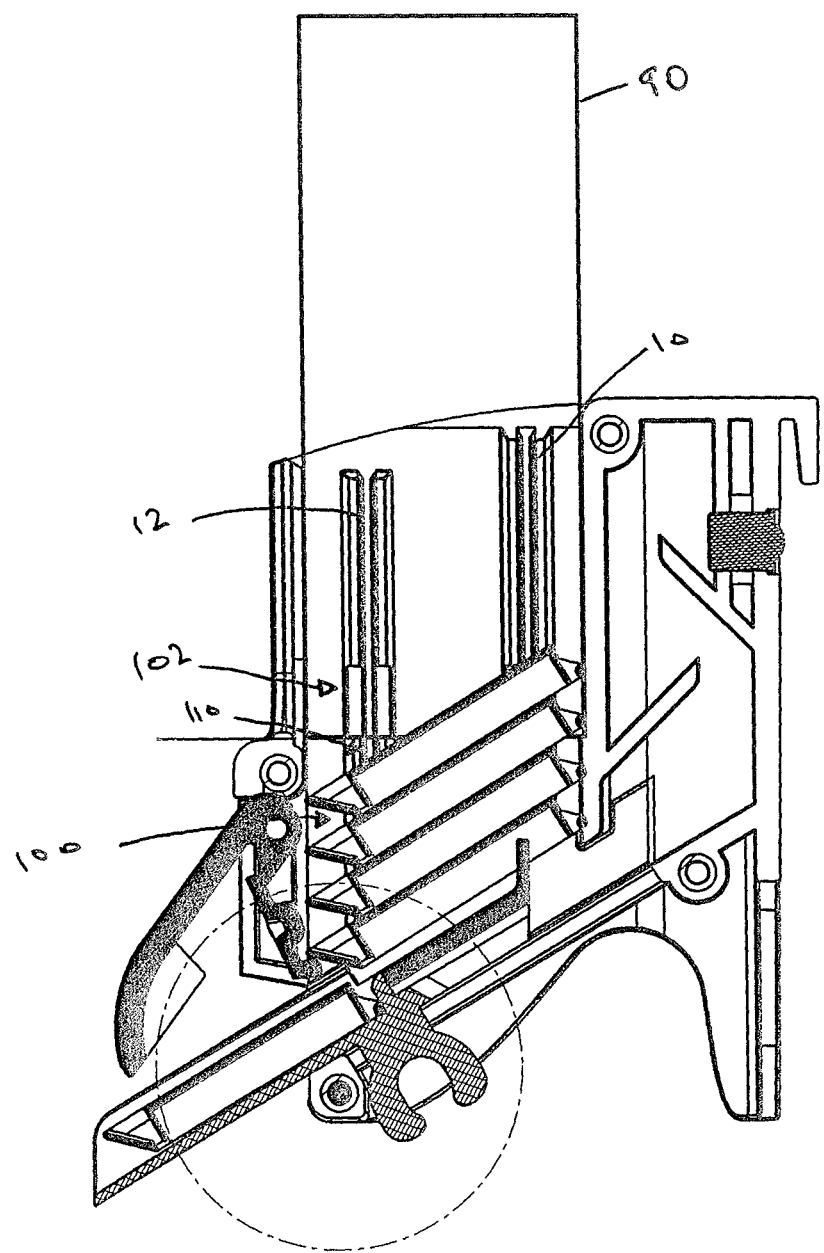
FIG. 10 is another view of the apparatus as seen in FIG. 8 but with a partially empty cassette tube in place.

FIG. 9a shows a sectional view to a dispensing apparatus in a similar state to that of FIG. 8 i.e. with the tray 18 fully extended. However, in FIG. 9a the apparatus is shown with a tissue cassette tube 90 in place. Also more cassettes (in this case 10) are shown remaining in the stack whilst a cassette is being dispensed. As previously explained, typically the cassettes are supplied in a cassette tube 90 and it is convenient simply to load the entire tube 90 into the hopper of the apparatus. However, the cassette tube 90 does not extend all the way to the bottom of the hopper, as can be seen in FIG. 10. Instead, the cassettes emerge from the lower end of the cassette tube 90 (e.g. under the action of gravity) into a pocket region 100 of the hopper, in this case at the lower end of the hopper.

As previously mentioned, the upper walls of the hopper are provided with protuberances 10, 12 (in this example, each item 10 and 12 consists of a pair of protuberances but any suitable number may be used). These protuberances serve to locate the cassette tube 90 in position and to hold it firmly. However, protuberances 10, 12 do not extend all the way down the side walls of the hopper continuously. Instead, in a region 102 adjacent the end of the cassette tube 90, the protuberances are reduced or even omitted altogether. As previously explained, this helps to permit the sides of the cassette tube 90 at its end to flex more easily and therefore to allow the cassettes to exit the tube 90.

The pocket region 100 of the hopper also includes protuberances. In FIG. 10, only part of protuberances 110 can be seen on one of the side walls of the pocket region. These protuberances can also be seen more clearly in FIGS. 5-9. However, in some embodiments, the side wall of the pocket region will include two protuberances, or even two pairs of protuberances, in a similar fashion to items 10 and 12 of the hopper. In addition, the opposite side wall of the hopper and/or pocket region may include similar side protuberances (not seen). Again, as previously explained, the protuberances 110 of the pocket region serve to hold the cassettes in the correct position once they have emerged or partially emerged from the tube 90. In order to accomplish this, in some embodiments, protuberances 110 may extend further away from the side wall of the pocket region than the similar protuberances 10, 12 extend from the side wall of the hopper.

Figure 9B:
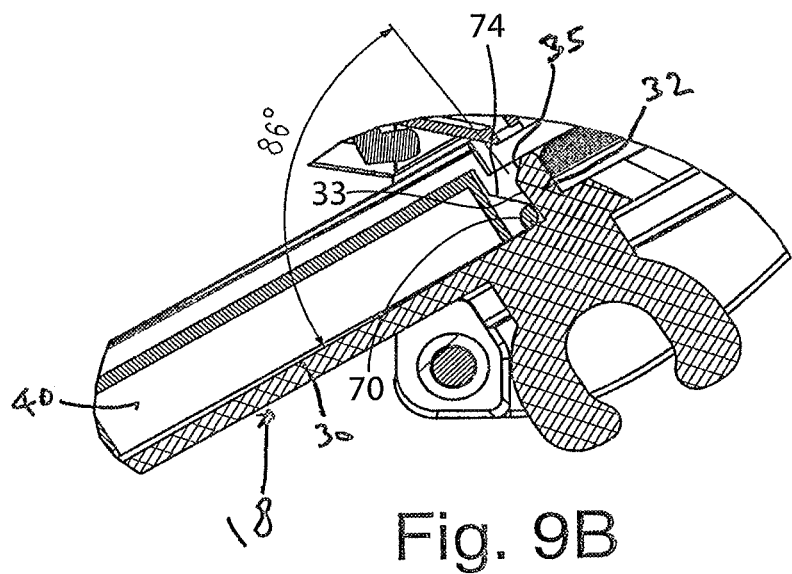
FIG. 9b is a detail from FIG. 9a showing the tray.

FIG. 9b shows a sectional view of the portion of the tray 18. This illustrates more clearly the nature of the rear wall 32 of the tray. In particular, according to one aspect of the invention, the inner face 33 of the rear wall 32 is not perpendicular to the base 30 of the tray. Preferably, a portion of it is inclined to the base at an acute angle, and in this example the angle shown is 86 degrees. However, that may be varied to e.g. between 80 and 89 degrees. The purpose of this is to help to grip the rear portion 74 of cassette 40 in the tray, to help prevent cassette 40 from lifting upwards out of the tray.

One optional additional feature of rear wall 32 of the tray 18 is that a second portion (the upper part 35) of inner face 33 may be angled in the opposite direction to the remainder of the inner face i.e. is at an obtuse angle to the base 30. If, in spite of the other features of the present invention, the rear of adjacent cassette 42 should drop down as the tray is being slid forward, then this upper portion 35 helps to push cassette 42 back into position, and away from cassette 40.

Figure 12:
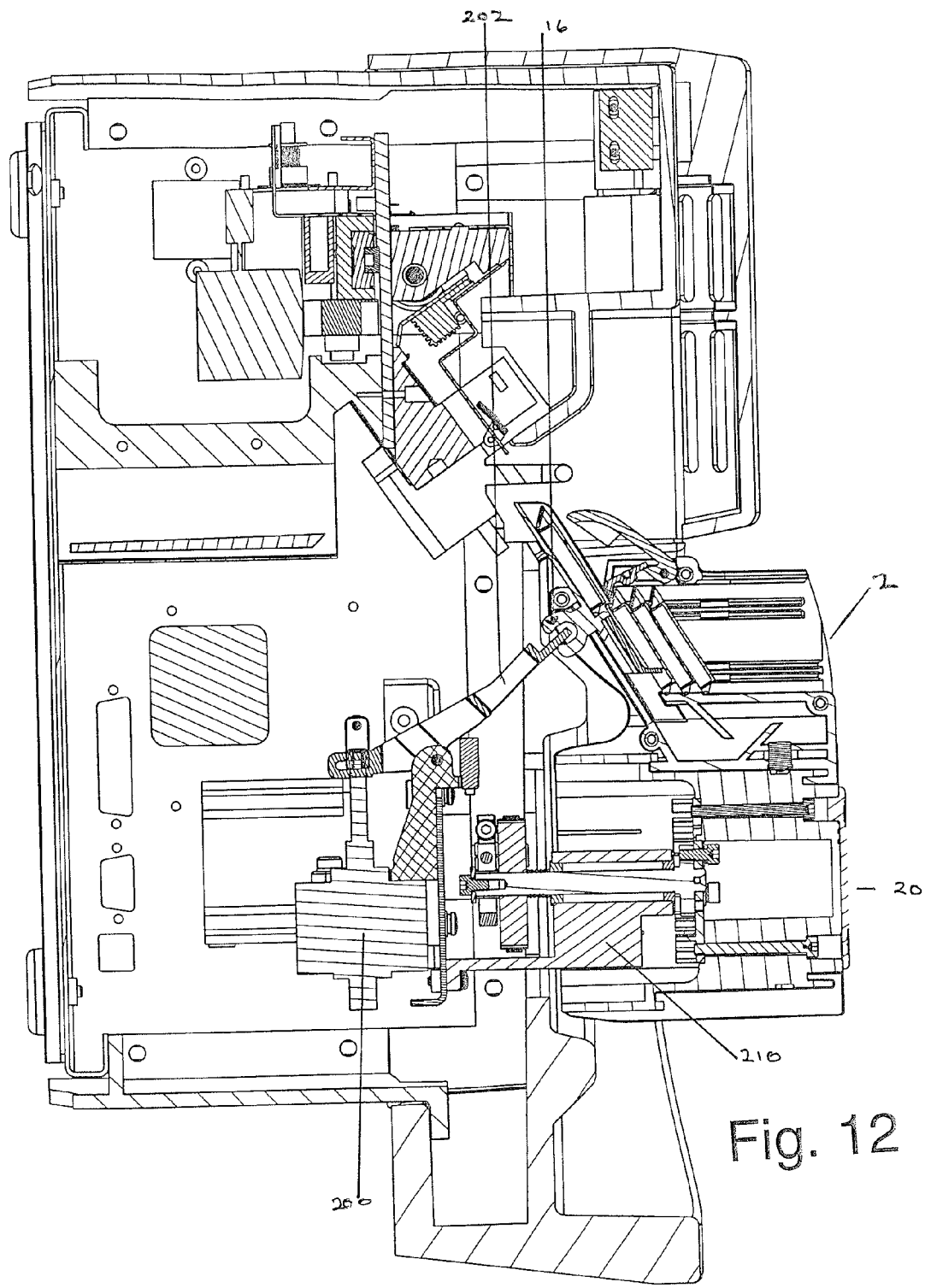
FIG. 12 shows a partial sectional view through a tissue cassette processing apparatus incorporation aspects of the present invention, including incorporating the dispensing apparatus of FIGS. 1-8.

FIG. 12 shows a sectional view though part of the tissue cassette processing apparatus of FIG. 11. This illustrates an ejection operation mechanism (generally 200) for operating the ejection means of a dispensing apparatus as previously described. It also shows an indexing mechanism (generally 210)(transport means) for operating the carousel 20 so as to bring a desired dispensing apparatus into the appropriate position so that a desired cassette can be dispensed. Ejection operation mechanism 200 includes a finger 202 which engages with engagement member 16 and is usable to move engagement member 16 to slide the tray of dispensing apparatus to as previously described.

The invention may include any variations, modifications and alternative applications of the above embodiments, as would be readily apparent to the skilled person without departing from the scope of the present invention in any of its aspects.

The invention claimed is:
1. A dispensing apparatus for dispensing individual tissue cassettes from a stack of such cassettes, the apparatus including:

a hopper for receiving a stack of tissue cassettes, the hopper having an aperture through which a lowermost one of the cassettes is dispensable;

an ejection device to eject the lowermost cassette through the aperture;

a retention device to retain all but the lowermost one of the cassettes in the stack as the lowermost cassette is ejected, the retention device including a support member that acts to support at least part of the weight of the stack as the lowermost cassette is ejected, the retention device thereby reducing the force exerted on the lowermost cassette by the weight of the stack as the lowermost cassette is ejected;

the hopper including a gate to close the aperture;

the retention device being arranged in conjunction with the gate such that when the gate is fully open the retention device is in operation to retain the remainder of the cassettes in the stack;

the ejection device including a tray in which the lowermost cassette may be held;

the tray being sloped and the gate being arranged so that in use, the gate prevents the lowermost cassette from sliding out of the tray under the action of gravity until the gate is fully open;

the tray including a separation device to improve the separation of the lowermost cassette held within the tray from an adjacent cassette as the tray is moved; and wherein a portion of an inner face of a rear wall of the tray is inclined relative to a base of the tray at an acute angle, so that when the lowermost cassette is in position in the tray an upper part of the portion of the inner face of the rear wall of the tray is nearer to the lowermost cassette than a lower part of the portion of the inner face of the rear wall of the tray.

2. A dispensing apparatus for dispensing individual tissue cassettes from a stack of such cassettes, the apparatus including:

a hopper for receiving a stack of tissue cassettes, the hopper having an aperture through which a lowermost one of the cassettes is dispensable;

an ejection device to eject the lowermost cassette through the aperture;

a retention device to retain all but the lowermost one of the cassettes in the stack as the lowermost cassette is ejected, the retention device including a support member that acts to support at least part of the weight of the stack as the lowermost cassette is ejected, the retention device thereby reducing the force exerted on the lowermost cassette by the weight of the stack as the lowermost cassette is ejected;

the hopper including a gate to close the aperture;

the retention device being arranged in conjunction with the gate such that when the gate means is fully open the retention device is in operation to retain the remainder of the cassettes in the stack;

the ejection device including a tray in which a single tissue lowermost cassette may be held, the tray further including a separation device to improve the separation of the lowermost cassette held within the tray from an adjacent cassette as the tray is moved, and wherein a portion of an inner face of a rear wall of the tray is inclined relative to a base of the tray at an acute angle, so that when the lowermost cassette is in position in the tray an upper part of the portion of the inner face of the rear wall of the tray is nearer to the lowermost cassette than a lower part of the portion of the inner face of the rear wall of the tray.

3. A dispensing apparatus according to claim 2 wherein the retention device includes a finger or tooth which is moveable so as to grip a cassette.

4. A dispensing apparatus according to claim 2 wherein the hopper includes a pocket region in which at least part of the stack of cassettes may be held in use.

5. A dispensing apparatus according to claim 4 wherein the support member of the retention device acts on one or more of the cassettes in the stack in the pocket region.

6. A dispensing apparatus according to claim 5 wherein the support member of the retention device acts on at least the lowest cassette in the pocket region, which when the at least the lowest cassette in the pocket region is retained in position in the pocket region by the retention device, then the at least the lowest cassette in the pocket region in turn serves to hold the remainder of the cassettes in the stack in position.

7. A dispensing apparatus according to claim 6 wherein the lowest cassette in the pocket region is the cassette next in the stack to the cassette in a tray of the ejection device.

8. A dispensing apparatus according to claim 2 wherein the tray is moveable so as to be useable to transport a lowermost cassette away from the stack of cassettes when a lowermost cassette is to be dispensed.

9. A dispensing apparatus according to claim 8, wherein the tray is slidable and wherein the sliding action of the tray opens the gate.

10. A dispensing apparatus according to claim 2 wherein the gate device is biased to a closed position.

11. A dispensing apparatus according to claim 2 wherein a second upper portion of the inner face of the rear wall of the tray is angled at an obtuse angle to the base of the tray, so that the upper part of the portion of the inner face of the rear wall of the tray that is inclined relative to the base of the tray at an acute angle is nearer to the lowermost cassette in the tray than an upper part of the second, upper portion of the inner face of the rear wall of the tray that is angled at an obtuse angle to the base of the tray.

12. A dispensing apparatus according to claim 2 wherein the opening of the gate device causes the retention device to operate.

13. A dispensing apparatus according to claim 2 wherein when the gate is fully closed, the retention device is not retaining the cassettes in the stack in any particular position.

14. A dispensing apparatus according to claim 2 wherein the gate includes a member which causes a finger or tooth of the retention device to engage one or more cassettes in the stack.

15. A dispensing apparatus according to claim 2 wherein the gate acts so as to prevent a cassette from leaving the tray unless the gate is fully open.

16. The dispensing apparatus of claim 2 configured to be removably mountable to a tissue cassette processing apparatus, the ejection device of the dispensing apparatus being configured to be operated by an ejection operating device of the tissue cassette processing apparatus.

* * * * *